United States Patent
Kawada et al.

(10) Patent No.: US 8,742,353 B2
(45) Date of Patent: Jun. 3, 2014

(54) SINGLE TERAHERTZ WAVE TIME-WAVEFORM MEASURING DEVICE

(75) Inventors: Yoichi Kawada, Hamamatsu (JP); Takashi Yasuda, Hamamatsu (JP); Hironori Takahashi, Hamamatsu (JP); Shinichiro Aoshima, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 1393 days.

(21) Appl. No.: 12/444,209

(22) PCT Filed: Sep. 13, 2007

(86) PCT No.: PCT/JP2007/067843
§ 371 (c)(1),
(2), (4) Date: Dec. 22, 2009

(87) PCT Pub. No.: WO2008/044424
PCT Pub. Date: Apr. 17, 2008

(65) Prior Publication Data
US 2010/0090112 A1    Apr. 15, 2010

(30) Foreign Application Priority Data
Oct. 10, 2006    (JP) .................................. 2006-276660

(51) Int. Cl.
*G01N 21/35*    (2014.01)

(52) U.S. Cl.
CPC ...................................... *G01N 21/35* (2013.01)
USPC ..................................... 250/338.4; 250/338.5

(58) Field of Classification Search
CPC ...................................................... G01N 21/35
USPC ....................... 250/338.4, 341.1, 341.8, 338.5
See application file for complete search history.

(56) References Cited

U.S. PATENT DOCUMENTS 6,573,700 B2 *    6/2003    Zhang et al. ..................... 324/96
2005/0253071 A1 *    11/2005    Ferguson et al. .......... 250/341.1
(Continued)

FOREIGN PATENT DOCUMENTS

JP    2006-64610    3/2006
WO    2006/085403    8/2006

OTHER PUBLICATIONS

Takashi Yasuda et al., "Real-time Two-dimensional Spatiotemporal Imaging for THz Tomography of a Moving Object," Optical Terahertz Science and Technology (OSA Topical Meeting), Orlando, Florida (USA), Mar. 14-16, Technical Digest (CD) TuC6, 2005.

(Continued)

*Primary Examiner* — David Porta
*Assistant Examiner* — Faye Boosalis
(74) *Attorney, Agent, or Firm* — Drinker Biddle & Reath LLP

(57) ABSTRACT

A single terahertz wave time-waveform measuring device 1 acquires information on an object to be measured 9 by using a terahertz wave, and includes a light source 11, a beam diameter adjuster 12, a separator 13, a terahertz wave generator 21, a light path length difference adjuster 31, a pulse front tilting unit 32, a polarizer 33, a wave synthesizer 41, an electro-optic crystal 42, an analyzer 43, and a photodetector 44. The terahertz wave generator 21 generates a pulse terahertz wave in response to an input of pump light and outputs the pulse terahertz wave. The pulse front tilting unit 32 makes pulse fronts of the terahertz wave and the probe light when being input into the electro-optic crystal 42 nonparallel to each other by tilting the pulse front of the probe light.

6 Claims, 14 Drawing Sheets

(56) References Cited

U.S. PATENT DOCUMENTS

2006/0231762 A1* 10/2006 Ohtake et al. ............. 250/341.8
2008/0265165 A1* 10/2008 Yeh et al. ................. 250/341.1

OTHER PUBLICATIONS

Zhiping Jiang et al., "Electro-optic measurement of THz field pulses with a chirped optical beam," Applied Physics Letters, Apr. 20, 1998, pp. 1945-1947, vol. 72, No. 16.

Zhiping Jiang et al., "Terahertz pulse measurement with an optical streak camera," Optics Letters, Sep. 1, 1999, pp. 1245-1247, vol. 24, No. 17.

Jie Shan et al., "Shingle-shot measurement of terahertz electromagnetic pulses by use of electro-optic sampling," Optics Letters, Mar. 15, 2000, pp. 426-428, vol. 25, No. 6.

Zhiping Jiang et al., "Measurement of Spatio-Temporal Terahertz Field Distribution by Using Chirped Pulse Technology," IEEE Journal of Quantum Electronics, Oct. 2000, pp. 1214-1222, vol. 36, No. 10.

Steven P. Jamison et al., "High-temporal-resolution, single-shot characterization of terahertz pulses," Optics Letters, Sep. 15, 2003, pp. 1710-1712, vol. 28, No. 18.

* cited by examiner

Fig.6
(a)
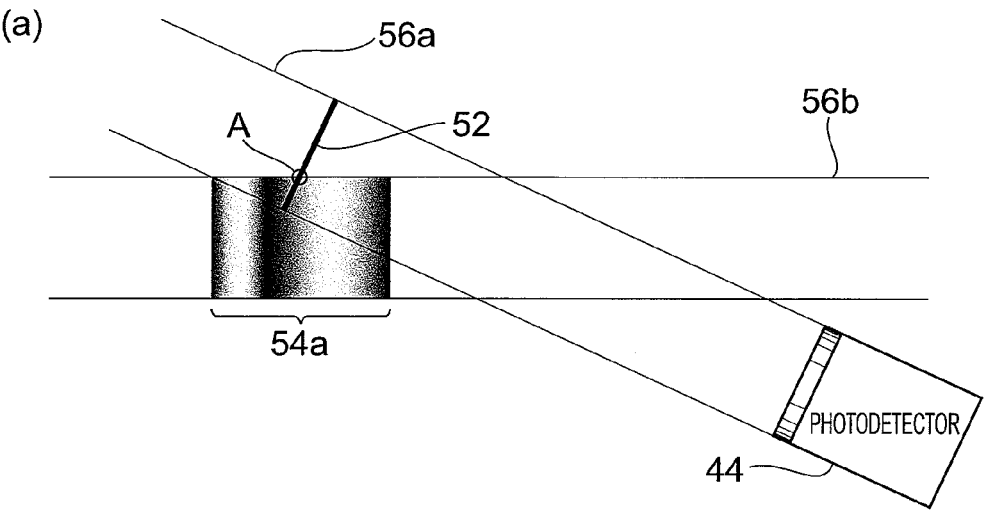
(b)
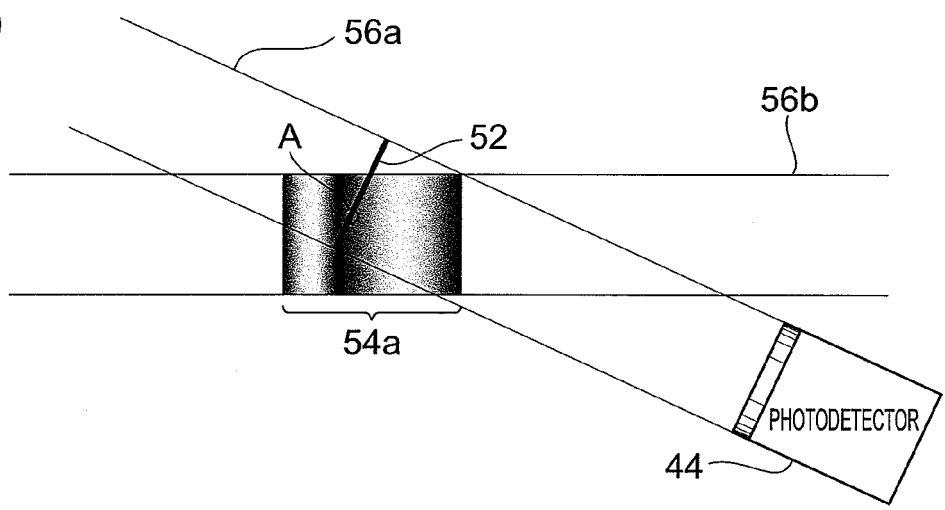
(c)
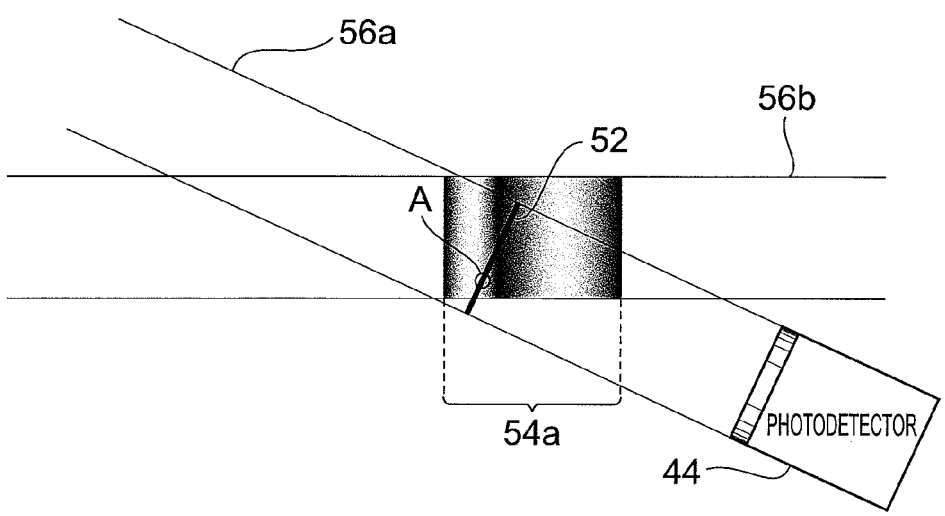

SINGLE TERAHERTZ WAVE TIME-WAVEFORM MEASURING DEVICE

TECHNICAL FIELD

The present invention relates to a device which measures a time waveform of a terahertz wave transmitted through or reflected by an object to be measured and evaluates characteristics of the object to be measured.

BACKGROUND ART

Terahertz waves are electromagnetic waves with a frequency of approximately 0.01 THz to 1000 THz corresponding to an intermediate region between light waves and radio waves, and have intermediate characteristics between light waves and radio waves. As application of such a terahertz wave, a technique for acquiring information on an object to be measured by measuring a time waveform of an electric field amplitude of a terahertz wave transmitted through or reflected by the object to be measured (refer to Non-patent documents 1 to 4) has been studied.

The measuring technique for information on an object to be measured by using a terahertz wave is generally as follows. That is, pulsed light output from a light source (for example, a femtosecond laser light source) is two-separated into a pump light and a probe light by a separator. The pump light of these is input into a terahertz wave generating nonlinear optical crystal, and accordingly, a pulse terahertz wave is generated from this nonlinear optical crystal. The generated terahertz wave is transmitted through or reflected by an object to be measured, and accordingly, information on the object to be measured (for example, an absorption coefficient, and a refractive index) are obtained, and thereafter, the wave is synthesized with the probe light by a wave synthesizer, and made incident on a terahertz wave detecting electro-optic crystal at a timing substantially synchronous with the probe light.

In the electro-optic crystal into which the terahertz wave and the probe light are input, birefringence is induced along with propagation of the terahertz wave, and the birefringence changes a polarized state of the probe light in the electro-optic crystal. Therefore, a polarizer is provided on the light path of the probe light between the separator and wave synthesizer, an analyzer is provided on the output side of the electro-optic crystal, and the intensity of probe light transmitted through the analyzer is detected, whereby polarized state changes of the probe light in the electro-optic crystal are detected, and eventually, an electric field amplitude of the terahertz wave is detected, and characteristics of the object to be measured are obtained. Thus, the measuring technique for information on an object to be measured by using a terahertz wave uses an electro-optic effect caused by a pulse terahertz wave on the terahertz wave detecting electro-optic crystal.

Generally, the pulse width of a terahertz wave is on the level of picoseconds, and on the other hand, the pulse width of probe light is on the level of femtoseconds, so that the pulse width of probe light is several digits smaller than that of a terahertz wave. Accordingly, by sweeping an incidence timing of the probe light on a terahertz wave detecting electro-optic crystal, a time waveform of an electric field amplitude of a pulse terahertz wave is obtained.

Non-patent document 1: Jie Shan, et al., Opt. Lett., Vol. 25, No. 6, pp. 426-428 (2000)

Non-patent document 2: Takashi Yasuda, et al., Optical Terahertz Science and Technology (OSA Topical Meeting), Orlando, USA, March 14-16, Technical Digest (CD) TuC6 (2005)

Non-patent document 3: Zhiping Jiang, et al., Appl. Phys. Lett. Vol. 72, No. 16, pp. 1945-1947 (1998)

Non-patent document 4: Zhiping Jiang, et al., Opt. Lett., Vol. 24, No. 16, pp. 1245-1947 (1999)

DISCLOSURE OF THE INVENTION

However, in the above-described measuring technique for information on an object to be measured, to obtain a time waveform of an electric field amplitude of a pulse terahertz wave, a number of pulsed lights are output from a light source, and for each pulse, an incidence timing of probe light on an electro-optic crystal must be set, so that the time necessary for this is long.

On the other hand, in the measuring technique for information on an object to be measured described in Non-patent document 1, a terahertz wave and probe light are made incident on the terahertz wave detecting electro-optic crystal from mutually different directions so that the terahertz wave and probe light intersect each other in the electro-optic crystal, whereby a time waveform of an electric field amplitude of a pulse terahertz wave is obtained from a single pulse.

However, depending on various conditions (the phase matching condition, the spatial layout, and the crystal size) relating to the terahertz wave detection principle, the electro-optic crystal limits the incidence angles of the terahertz wave and probe light on the electro-optic crystal. Further, due to oblique incidence on the electro-optic crystal, the time waveform of the electric field amplitude of the detected pulse terahertz wave becomes inaccurate in principle, and time resolution is deteriorated.

The present invention was made for solving the above-described problem, and an object thereof is to provide a single terahertz wave time-waveform measuring device which can measure a time waveform of an electric field amplitude of a pulse terahertz wave in a short time with high time resolution.

Means for Solving the Problem

A single terahertz wave time-waveform measuring device of the present invention includes: (1) a light source which outputs pulsed light; (2) a separator which two-separates the pulsed light output from the light source and outputs either of the two-separated pulsed lights as a pump light and the other as a probe light; (3) a terahertz wave generator which generates a terahertz wave in response to an input of the pump light output from the separator; (4) a wave synthesizer which receives an input of a terahertz wave which was output from the terahertz wave generator and transmitted through or reflected by an object to be measured and the probe light which was output from the separator and reached, and synthesizes coaxially and outputs these terahertz wave and the probe light; (5) an electro-optic crystal which receives inputs of the terahertz wave and probe light output from the wave synthesizer, induces birefringence along with propagation of the terahertz wave, and changes a polarized state of the probe light by the birefringence and outputs the probe light; (6) a pulse-front tilting unit which makes pulse fronts of the terahertz wave and probe light when being input into the electro-optic crystal nonparallel to each other by tilting the pulse front of any of the pump light, the terahertz wave, and the probe light; and (7) a detecting device which detects a distribution of polarized state changes on a beam cross-section of the probe light output from the electro-optic crystal.

In this single terahertz wave time-waveform measuring device, the pulsed light output from the light source is two-separated by the separator, and one of the two-separated pulsed lights is used as a pump light, and the other is used as a probe light. The pump light output from the separator is input into the terahertz wave generator, and accordingly, a terahertz wave is output from the terahertz wave generator. The terahertz wave which was output from the terahertz wave generator and transmitted through or reflected by an object to be measured and the probe light which was output from the separator are synthesized coaxially and output by the wave synthesizer. When the terahertz wave and probe light output from the wave synthesizer are input into the electro-optic crystal, in the electro-optic crystal, along with propagation of the terahertz wave, birefringence is induced, and a polarized state of the probe light is changed by birefringence and then the probe light is output. By the pulse-front tilting unit, a pulse-front of any of the pump light, the terahertz wave, and the probe light is tilted so that the pulse-fronts of the terahertz wave and probe light when being input into the electro-optic crystal are made nonparallel to each other. Then, by the detecting device, a distribution of polarized state changes on the beam cross-section of the probe light output from the electro-optic crystal is detected.

More preferably, the single terahertz wave time-waveform measuring device further includes a light path length difference adjuster which adjusts a difference between a light path of the pump light and terahertz wave from the separator to the wave synthesizer and a light path of the probe light from the separator to the wave synthesizer. Preferably, the single terahertz wave time-waveform measuring device further includes a beam diameter adjuster which adjusts both or either of beam diameters of the terahertz wave and the probe light when being input into the electro-optic crystal.

In the single terahertz wave time-waveform measuring device, preferably, (1) the pulse-front tilting unit changes time delay caused by a tilt of the pulse front of either of the terahertz wave and the probe light when being input into the electro-optic crystal along a predetermined direction on a beam cross-section, and (2) the detecting device detects one-dimensional distribution of the polarized state changes along the predetermined direction on the beam cross-section of the probe light output from the electro-optic crystal. Also, in the single terahertz wave time-waveform measuring device, preferably, (1) the pulse-front tilting unit changes time delay caused by a tilt of the pulse front of either of the terahertz wave and the probe light when being input into the electro-optic crystal along a first direction and a second direction orthogonal to each other on a beam cross-section, respectively, and (2) the detecting device detects a two-dimensional distribution of the polarized state changes along the first direction and the second direction on the beam cross-section of the probe light output from the electro-optic crystal.

Here, "time delay caused by a tilt of the pulse front" means temporal deviation between the pulse front of the terahertz wave and the pulse front of the probe light. In other words, according to tilting of the pulse front of either the terahertz wave or the probe light, the "time delay caused by a tilt of the pulse front" on the pulse front at each position on the beam cross-section spreads, and a time window described later is expanded.

Preferably, the single terahertz wave time-waveform measuring device further includes a condenser which condenses and irradiates a terahertz wave output from the terahertz wave generator in a line onto an object to be measured; and a collimator which collimates a terahertz wave transmitted through or reflected by the object to be measured and outputs it to the wave synthesizer. As the condenser or collimator, a cylindrical lens is preferably used. The terahertz wave irradiated onto the object to be measured from the condenser may be collimated by the collimator after being transmitted through the object to be measured, or may be collimated by the collimator after being reflected by the object to be measured. In the latter reflection case, an optical component (for example, a cylindrical lens) can be used commonly as the condenser and collimator. Also preferably, the object to be measured which was irradiated with the terahertz wave condensed in a line by the condenser is scanned in a direction perpendicular to the line.

Effect of the Invention

According to the present invention, a time waveform of an electric field amplitude of a pulse terahertz wave can be measured in a short time with high time resolution.

BRIEF DESCRIPTION OF THE DRAWINGS

[FIG. 6] is a view describing a problem in measurement with the single terahertz wave time-waveform measuring device 102 of the second configuration example;

DESCRIPTION OF REFERENCE NUMERALS

Figure 1:
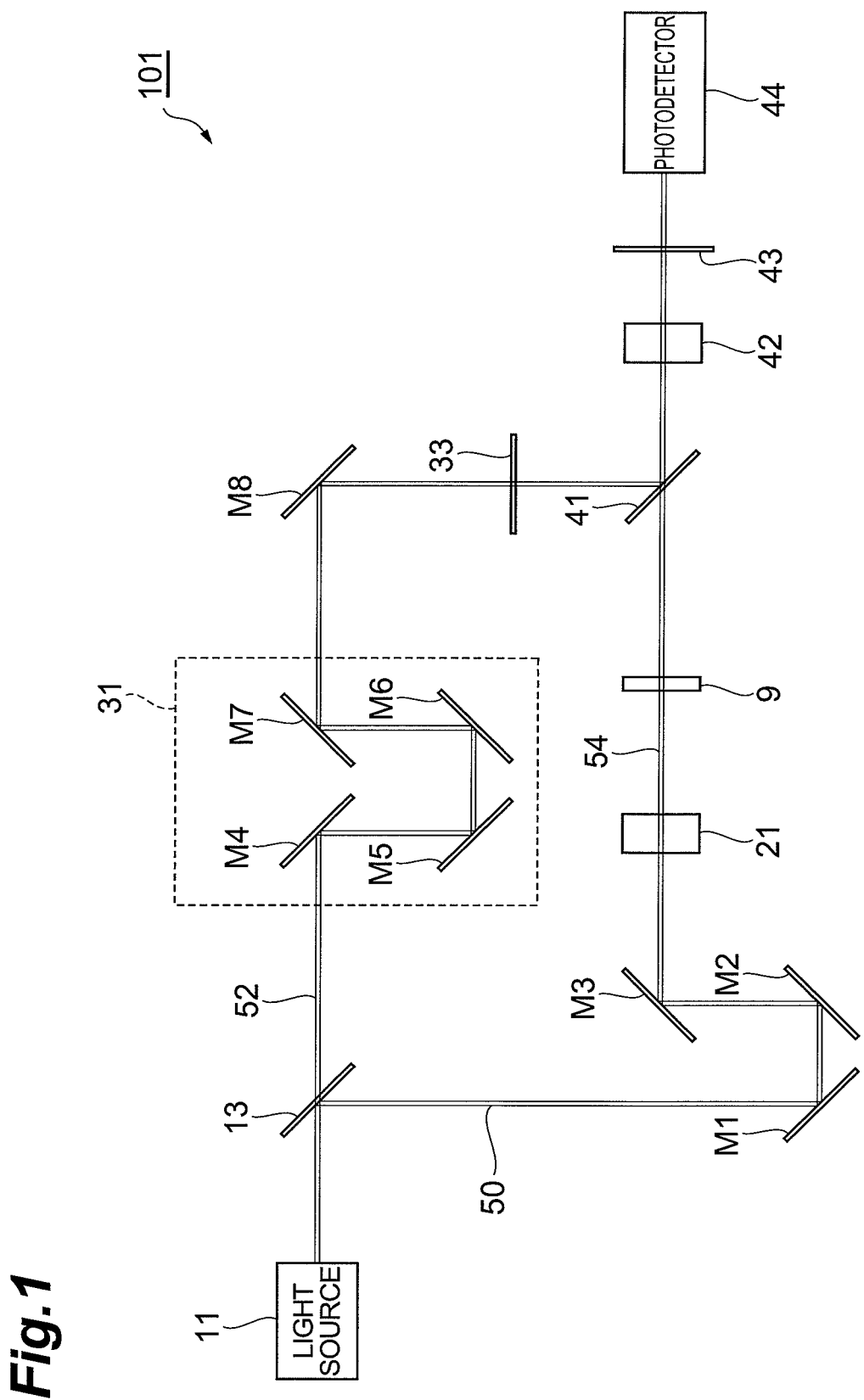
[FIG. 1] is a configuration view of a terahertz wave time-waveform measuring device 101 of a first configuration example.

1: Terahertz wave time-waveform measuring device, 2 to 4: Single terahertz wave time-waveform measuring device, 9:

9: Object to be measured, 11: Light source, 12: Beam diameter adjuster, 13: Separator, 21: Terahertz wave generator, 22: Cylindrical lens, 23: Prism, 24: Pulse front tilting unit, 25, 26: Lens, 31: Light path length difference adjuster, 32: Pulse front tilting unit, 33: Polarizer, 41: Wave synthesizer, 42: Electrooptic crystal, 43: Analyzer, 44: Photodetector, M1 to M8: Mirror

BEST MODES FOR CARRYING OUT THE INVENTION

Hereafter, best modes for carrying out the present invention will be described in detail with reference to the accompanying drawings. In description of the drawings, identical elements are attached with the same reference numeral, and overlapping description is omitted. Hereinafter, a first configuration example and a second configuration example will be described first, and thereafter, in comparison with these configuration examples, configurations of embodiments will be described.

FIRST CONFIGURATION EXAMPLE

FIG. 1 is a configuration view of a terahertz wave time-waveform measuring device 101 of a first configuration example. The terahertz wave time-waveform measuring device shown in this figure obtains information on an object to be measured 9 by using a terahertz wave, and includes a light source 11, a separator 13, a terahertz wave generator 21, an optical path length difference adjuster 31, a polarizer 33, a wave synthesizer 41, an electro-optic crystal 42, an analyzer 43, a photodetector 44, and mirrors M1 to M8.

The light source 11 outputs pulsed light with a predetermined cycle period, and is preferably a femtosecond pulse laser light source which outputs a pulsed laser beam having a pulse width of femtoseconds. The separator 13 is, for example, a beam splitter, and two-separates pulsed light output from the light source 11 and outputs either of the two-separated pulsed lights as a pump light 50 to the mirror M1 and the other as a probe light 52 to the mirror M4.

The pump light 50 output from the separator 13 is reflected by the mirrors M1 to M3 in order, and input into the terahertz wave generator 21. The optical system for the pump light from the separator 13 to the terahertz wave generator 21 is referred to as "a pump optical system," hereinafter.

The terahertz wave generator 21 generates a pulse terahertz wave (terahertz wave 54) in response to an input of the pump light 50, and includes, for example, any of a nonlinear optical crystal, an optical antenna element, and a semiconductor and a superconductor. When the terahertz wave generator 21 includes a nonlinear optical crystal, this terahertz wave generator 21 can generate a terahertz wave by a nonlinear optical phenomenon occurring along with pump light incidence.

Terahertz waves are electromagnetic waves having a frequency of approximately 0.01 THz to 1000 THz corresponding to an intermediate region between light waves and radio waves, and have intermediate characteristics between light waves and radio waves. A pulse terahertz wave is generated with a fixed cycle period, and has a pulse width of several picoseconds. The terahertz wave 54 output from the terahertz wave generator 21 is transmitted through the object to be measured 9, whereby information on the object to be measured (for example, an absorption coefficient and a refractive index) are acquired, and thereafter, the terahertz wave is input into the wave synthesizer 41. The optical system for the terahertz wave from the terahertz wave generator 21 to the wave synthesizer 41 is referred to as a "terahertz wave optical system," hereinafter.

On the other hand, the probe light 52 output from the separator 13 is reflected by the mirrors M4 to M8 in order, passes through the polarizer 33, and is then input in the wave synthesizer 41. The optical system for the probe light from the separator 13 to the wave synthesizer 41 is referred to as a "probe optical system," hereinafter.

The four mirrors M4 to M7 compose a light path length difference adjuster 31. In other words, by movement of the mirrors M5 and M6, the light path lengths between the mirror M4 and the mirror M7 and between the mirror M5 and the mirror M6 are adjusted, whereby the light path length of the probe optical system is adjusted. Accordingly, the light path length difference adjuster 31 can adjust the difference between the light path of the pump optical system and the terahertz wave optical system from the separator 13 to the wave synthesizer 41 and the light path of the probe optical system from the separator 13 to the wave synthesizer 41.

The wave synthesizer 41 receives inputs of a terahertz wave which was output from the terahertz wave generator 21 and transmitted through the object to be measured 9 and a probe light which was output from the separator 13 and reached the wave synthesizer 41, and synthesizes these terahertz wave and probe light coaxially and outputs these to the electro-optic crystal 42. This wave synthesizer 41 is preferably a pellicle.

The electro-optic crystal 42 receives an input of the terahertz wave and probe light output from the wave synthesizer 41, induces birefringence along with propagation of the terahertz wave, and changes a polarized state of the probe light by the birefringence and outputs the probe light to the analyzer 43. The photodetector 44 receives the probe light which was output from the electro-optic crystal 42 and passed through the analyzer 43 and detects the intensity of the received probe light. The polarizer 33, the analyzer 43, and the photodetector 44 operate as a detecting device which detects the polarized state changes of the probe light output from the electro-optic crystal 42.

This terahertz wave time-waveform measuring device 101 works as described below. The pulsed light output from the light source 11 is two-separated by the separator 13 into a pump light 50 and a probe light 52. The pump light 50 output from the separator 13 is reflected by the mirrors M1 to M3 in order and input into the terahertz wave generator 21. In the terahertz wave generator 21, a terahertz wave 54 is generated and output in response to the input of the pump light 50. The terahertz wave 54 output from the terahertz wave generator 21 is transmitted through the object to be measured 9 and input into the wave synthesizer 41. On the other hand, the probe light 52 output from the separator 13 is reflected by the mirrors M4 to M8 in order and converted into a linearly-polarized light from the polarizer 33 and input into the wave synthesizer 41.

The terahertz wave and the probe light input in the wave synthesizer 41 are synthesized coaxially by the wave synthesizer 41, and input into the electro-optic crystal 42 at substantially the same timing. In the electro-optic crystal 42 into which the terahertz wave and the probe light have been input, along with propagation of the terahertz wave, birefringence is induced, and this birefringence changes a polarized state of the probe light. The polarized state of the probe light in the electro-optic crystal 42 is detected as a light intensity by the polarizer 33 provided on the light path of the probe optical system, the analyzer 43 provided on the output side of the electro-optic crystal 42, and the photodetector 44 which detects the intensity of the probe light transmitted through the analyzer 43. Thus, polarized state changes of the probe light in the electro-optic crystal 42 are detected, and eventually, an electric field amplitude of the terahertz wave is detected, and characteristics of the object to be measured 9 are obtained.

Figure 2:
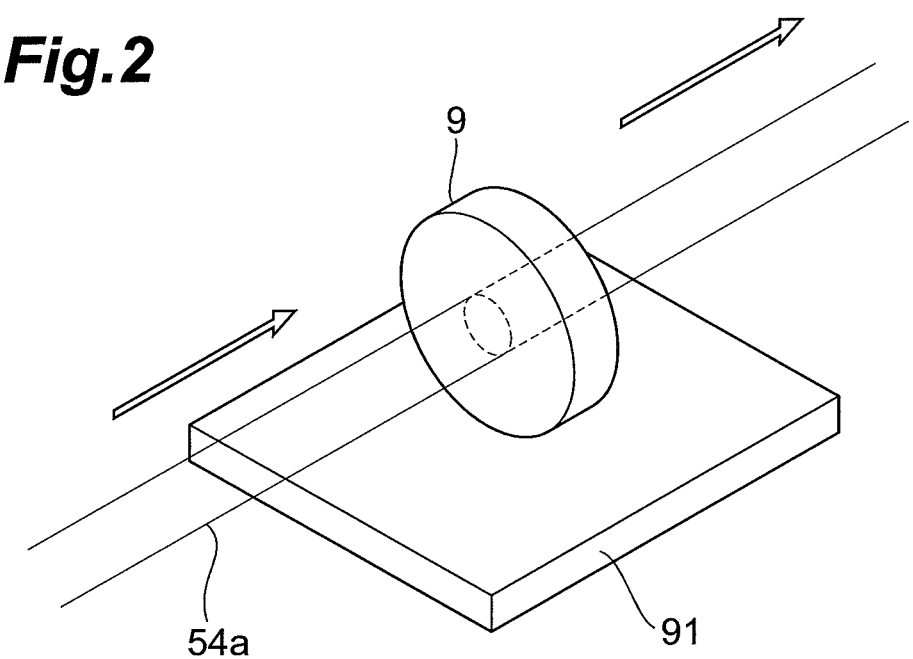
[FIG. 2] is a view showing transmission of a terahertz wave through an object to be measured 9.

FIG. 2 is a view showing transmission of the terahertz wave (pulse terahertz wave 54a) through the object to be measured 9. As shown in this figure, the object to be measured 9 is placed on a sample stage 91, and by moving the sample stage 91, the pulse terahertz wave incidence position can be adjusted.

Figure 3:
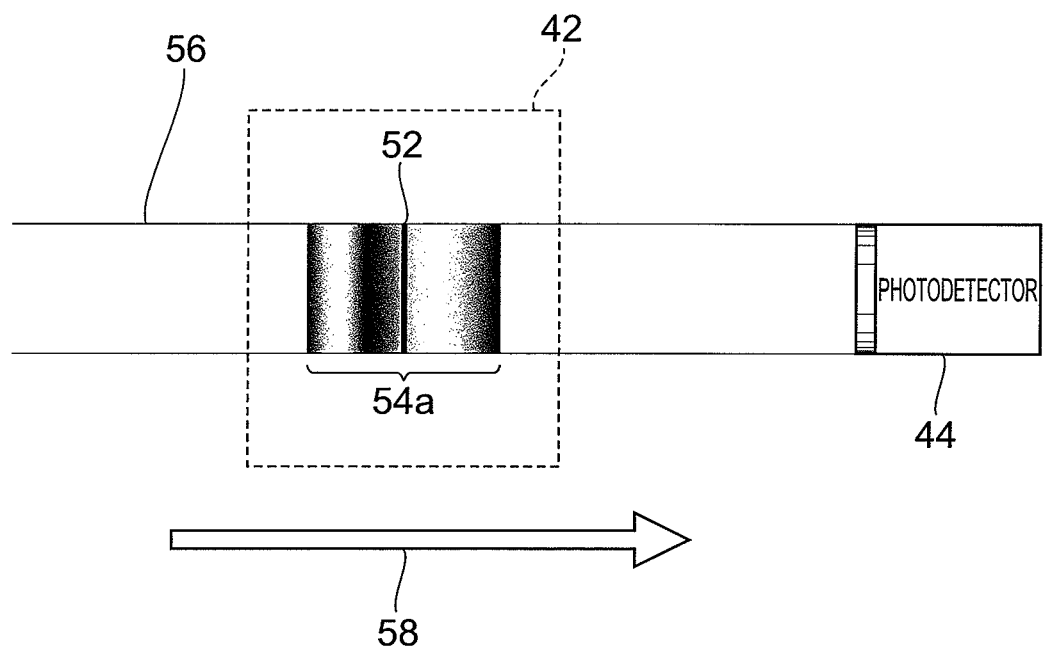
[FIG. 3] is a view showing propagation of a terahertz wave and probe light in an electro-optic crystal 42 included in the terahertz wave time-waveform measuring device 101 of the first configuration example.
Figure 4:
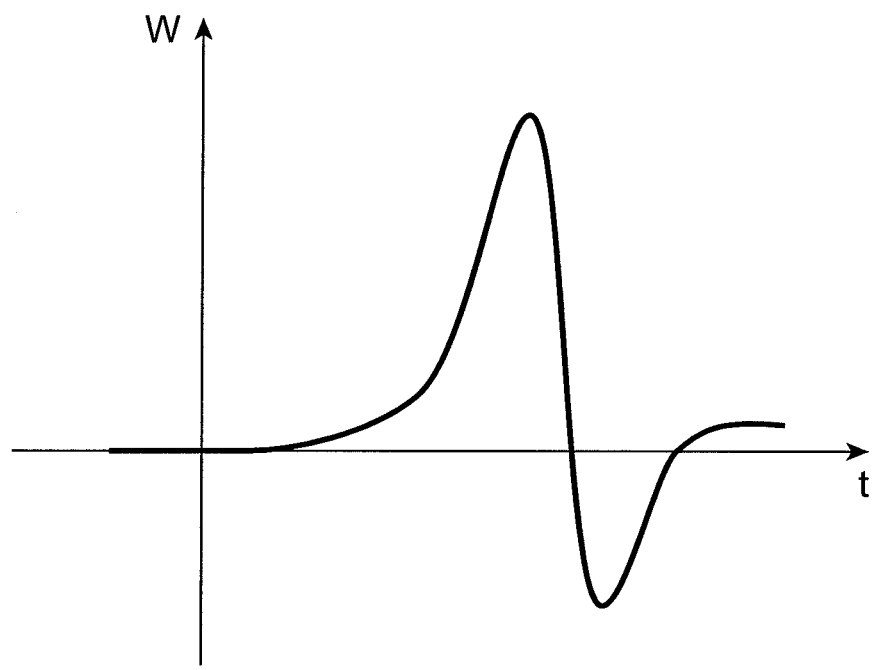
[FIG. 4] is a view showing an example of a time waveform of an electric field amplitude of a pulse terahertz wave.

FIG. 3 is a view showing propagation of the terahertz wave and the probe light in the electro-optic crystal 42 included in the terahertz wave time-waveform measuring device 101 of the first configuration example. The pulse terahertz wave 54a and the probe light 52 propagate along a propagation direction 58, and forms a beam line 56 of the probe light and pulse terahertz wave. As shown in this figure, the pulse width of the terahertz wave (pulse terahertz wave 54a) is on the level of picoseconds, and on the other hand, the pulse width of the probe light 52 is on the level of femtoseconds, and the pulse width of the probe light is several digits smaller than that of the terahertz wave. Therefore, only a small portion of the probe light with the narrow pulse width can be read in comparison with the duration of the terahertz wave with the wide pulse width. Therefore, by adjusting the light path length of the probe optical system by the light path length adjuster 31, the incidence timing, of the probe light on the terahertz wave detecting electro-optic crystal 42 is swept, and accordingly, a time waveform of the electric field amplitude of the pulse terahertz wave as shown in FIG. 4 is obtained. In FIG. 4, the vertical axis indicates the amplitude W and the horizontal axis indicates the time t.

However, in this terahertz wave time-waveform measuring device 101, to obtain a time waveform of the electric field amplitude of the pulse terahertz wave, it is necessary that a number of pulsed lights are output from the light source 11, and for each pulse, the incidence timing of the probe light on the electro-optic crystal 42 is set, so that the time necessary for this is long.

SECOND CONFIGURATION EXAMPLE

Figure 5:
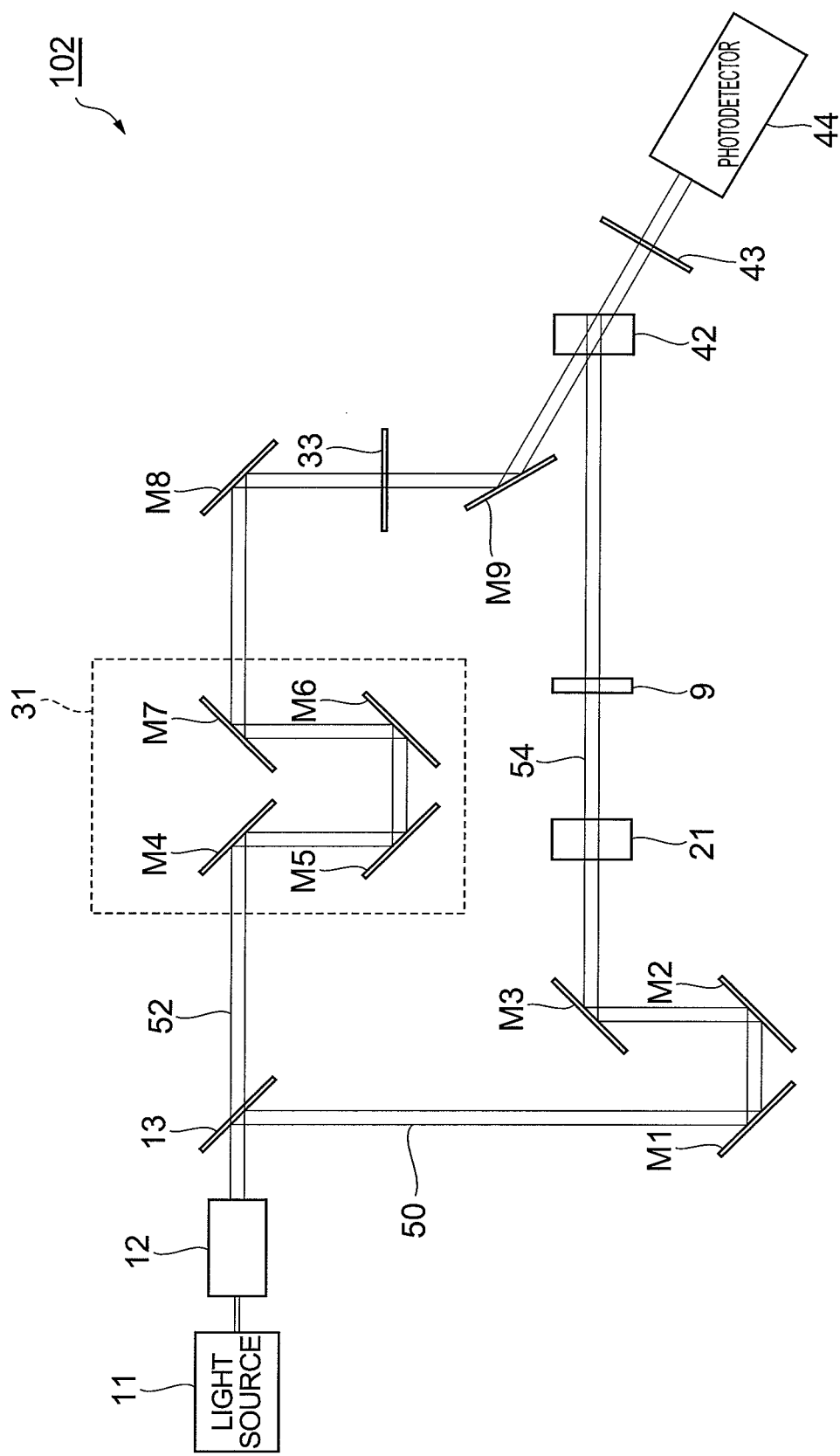
[FIG. 5] is a configuration view of a single terahertz wave time-waveform measuring device 102 of a second configuration example.

FIG. 5 is a configuration view of a single terahertz wave time-waveform measuring device 102 of a second configuration example. The single terahertz wave time-waveform measuring device 102 shown in this figure acquires information on an object to be measured 9 by using a terahertz wave, and includes a light source 11, a beam diameter adjuster 12, a separator 13, a terahertz wave generator 21, a light path length difference adjuster 31, a polarizer 33, an electro-optic crystal 42, an analyzer 43, a photodetector 44, and mirrors M1 to M9.

In comparison with the configuration of the terahertz wave time-waveform measuring device 101 of the first configuration example shown in FIG. 1, the single terahertz wave time-waveform measuring device 102 of the second configuration example shown in FIG. 5 is different in that a beam diameter adjuster 12 is provided on the light path between the light source 11 and the separator 13, the wave synthesizer 41 is not provided, a mirror M9 is further provided on the light path of the probe light 52 between the polarizer 33 and the electro-optic crystal 42, the terahertz wave and the probe light 52 are made incident on the electro-optic crystal 42 from mutually different directions, and a photodetector 44 which can detect a one-dimensional light intensity distribution is used.

This single terahertz wave time-waveform measuring device 102 works as follows. Pulsed light output from the light source 11 is expanded in beam diameter by the beam diameter adjuster 12 and then input into the separator 13, and two-separated by the separator 13 into a pump light 50 and a probe light 52. The pump light 50 output from the separator 13 is reflected by the mirrors M1 to M3 in order and input into the terahertz wave generator 21. In the terahertz wave generator 21, in response to an input of the pump light 50, a terahertz wave 54 is generated and output. The terahertz wave 54 output from the terahertz wave generator 21 is transmitted through the object to be measured 9 and input into the electro-optic crystal 42. On the other hand, the probe light 52 output from the separator 13 is reflected by the mirrors M4 to M8 in order, linearly polarized by the polarizer 33, and further, reflected by the mirror M9 and input into the electro-optic crystal 42.

The terahertz wave and the probe light are input into the electro-optic crystal 42 at substantially the same timing from mutually different directions. In the electro-optic crystal 42 into which the terahertz wave and the probe light have been input, birefringence is induced along with propagation of the terahertz wave, and the birefringence changes the polarized state of the probe light. This polarized state of the probe light in the electro-optic crystal 42 is detected as a light intensity by the polarizer 33 provided on the light path of the probe optical system, the analyzer 43 provided on the output side of the electro-optic crystal 42, and the photodetector 44 which detects the intensity of the probe light transmitted through the analyzer 43. Thus, the polarized state changes of the probe light in the electro-optic crystal 42 are detected, and eventually, an electric field amplitude of the terahertz wave is detected, whereby characteristics of the object to be measured 9 are obtained.

Particularly, in this single terahertz wave time-waveform measuring device 102, the pulse terahertz wave is readout with the probe light expanded in beam diameter. In other words, temporal information of the pulse terahertz wave is converted into spatial information of the probe light, and the spatial information of the probe light is detected by the photodetector 44.

The configuration of this single terahertz wave time-waveform measuring device 102 does not become complicated except that the photodetector 44 which can detect a one-dimensional light intensity distribution is used. On the other hand, when obtaining a time waveform of the electric field amplitude of the pulse terahertz wave, only a single pulse is used, so that the time necessary for this is short. However, depending on the various conditions relating to the terahertz wave detection principle (phase matching condition, spatial layout, and crystal size), the electro-optic crystal 42 limits the incidence angles of the terahertz wave and the probe light on the electro-optic crystal 42. Due to oblique incidence on the electro-optic crystal 42, the time waveform of the electric field amplitude of the detected pulse terahertz wave becomes inaccurate in principle, and the time resolution is deteriorated. This will be described with reference to FIG. 6.

FIG. 6 is a view describing a problem in measurement with the single terahertz wave time-waveform measuring device 102 of a second configuration example. FIG. 6a to FIG. 6c show intersections of the terahertz wave (pulse terahertz wave 54a) and the probe light 52 at times in order of drawings. In the propagation direction of the probe light 52, a beam line 56a of the probe light is formed. In the propagation direction of the pulse terahertz wave 54a, a beam line 56b of the pulse terahertz wave is formed. In FIG. 6a to FIG. 6c, a time waveform of the electric field amplitude of the terahertz wave as shown in FIG. 4 is expressed by a shading pattern. The points A shown in FIG. 6a to FIG. 6c shows the same point on the beam cross-section of the probe light 52. As seen in FIG. 6a to FIG. 6c in order, the same point A on the beam cross-section of the probe light 52 is at different positions in the time waveform of the electric field amplitude of the terahertz wave (pulse terahertz wave 54a) with elapse of time. The light intensity distribution detected by the one-dimensional photodetector 44 is influenced by all of these points. Accordingly, the time waveform becomes inaccurate and the time resolution is deteriorated.

(First Embodiment)

Figure 7:
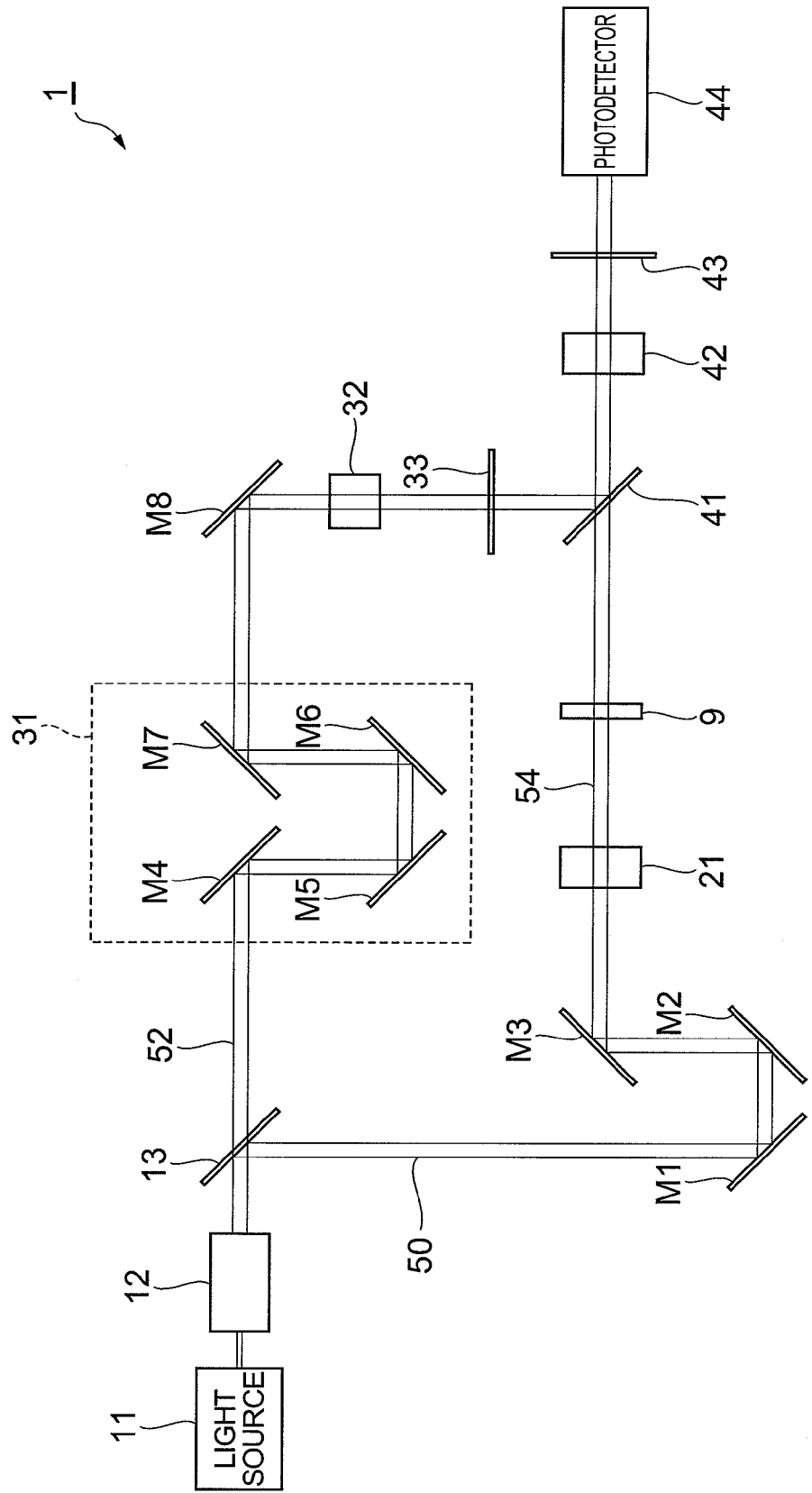
[FIG. 7] is a configuration view of a single terahertz wave time-waveform measuring device 1 of a first embodiment.

Next, a first embodiment of a single terahertz wave time-waveform measuring device of the present invention will be described. FIG. 7 is a configuration view of the single terahertz wave time-waveform measuring device 1 of the first embodiment. The single terahertz wave time-waveform measuring device 1 shown in this figure acquires information on the object to be measured 9 by using a terahertz wave, and includes a light source 11, a beam diameter adjuster 12, a separator 13, a terahertz wave generator 21, a light path length difference adjuster 31, a pulse front tilting unit 32, a polarizer 33, a wave synthesizer 41, an electro-optic crystal 42, an analyzer 43, a photodetector 44, and mirrors M1 to M8.

In comparison with the configuration of the terahertz wave time-waveform measuring device 101 of the first configuration example shown in FIG. 1, the single terahertz wave time-waveform measuring device of the first embodiment shown in FIG. 7 is different in that the beam diameter adjuster 12 is provided on the light path between the light source 11 and the separator 13, the pulse front tilting unit 32 is provided on the light path of the probe optical system, and a photodetector 44 which can detect a one-dimensional or two-dimensional light intensity distribution is used.

The beam diameter adjuster 12 receives an input of pulsed light output from the light source 11 and expands the beam diameter of the pulsed light and outputs it. In this beam diameter expanding adjustment, preferably, beam diameters of the terahertz wave and the probe light are made equal to each other, or the beam diameter of the terahertz wave is made larger than that of the probe light. These beam diameters are expanded by using the sizes of the terahertz wave generator 21 and the electro-optic crystal 42 as a standard.

Along with (or instead of) the beam diameter adjuster 12 provided on the light path between the light source 11 and the separator 13, a beam diameter adjuster which is provided on the light path of the pump optical system and adjusts the beam diameter of the pump light may be provided, a beam diameter adjuster which is provided on the light path of the probe optical system and adjusts the beam diameter of the probe light may be provided, or a beam diameter adjuster which is provided on the light path of the terahertz wave optical system and adjusts the beam diameter of the terahertz wave may be provided. The beam diameter adjuster adjusts both or either of the beam diameters of the terahertz wave and the probe light when being input into the electro-optic crystal 42.

The pulse front tilting unit 32 receives an input of the probe light 52 which was reflected by the mirror M8 and reached, tilts the pulse front of the probe light 52, and makes the pulse fronts of the terahertz wave and the probe light when being input into the electro-optic crystal 42 nonparallel to each other. The pulse front is a plane connecting positions of maximum outputs on the beam line of the pulsed light at a certain moment. On the other hand, wavefront means an iso-phase plane of light.

Along with (or instead of) the pulse front tilting unit 32 provided on the light path of the probe optical system, a pulse front tilting unit which is provided on the light path of the pump optical system and tilts the pulse front of the pump light may be provided, or a pulse front tilting unit which is provided on the light path of the terahertz wave optical system and tilts the pulse front of the terahertz wave may be provided. The pulse front tilting unit tilts the pulse front of any of the pump light, the terahertz wave, and the probe light to make the pulse fronts of the terahertz wave and the probe light when being input into the electro-optic crystal 42 nonparallel to each other.

The detecting device including the polarizer 33, the analyzer 43, and the photodetector 44 detects polarized state changes of the probe light output from the electro-optic crystal 42, and in particular, in the present embodiment, it detects a one-dimensional or two-dimensional distribution of the polarized state changes on the beam cross-section of the probe light output from the electro-optic crystal 42.

Figure 8:
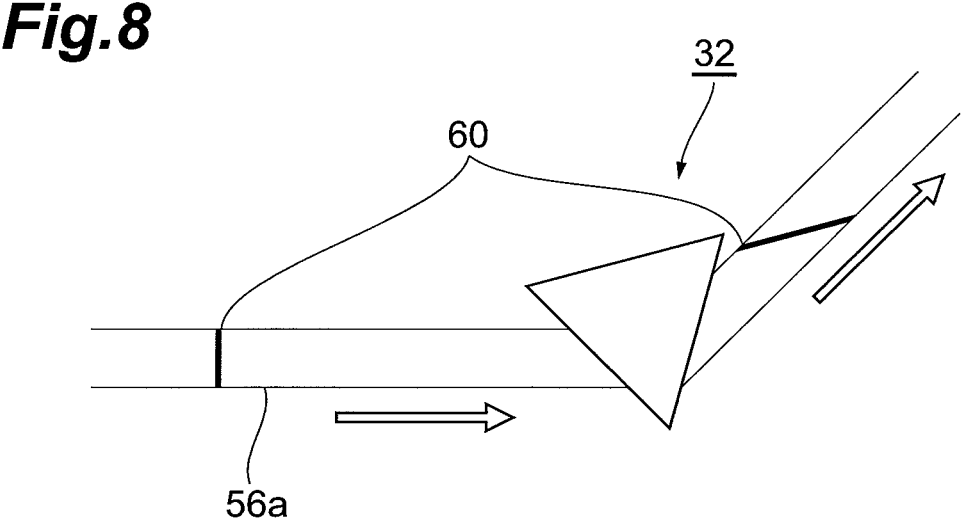
[FIG. 8] is a view showing a configuration example of a pulse front tilting unit 32.

FIG. 8 is a view showing a configuration example of the pulse front tilting unit 32. The pulse front tilting unit 32 shown in this figure includes a prism, and inputs the probe light into the first surface of the prism and propagates the input probe light inside the prism, and then outputs it to the outside from the second surface of the prism. Accordingly, the pulse front 60 of the probe light before being input into the first surface of the prism is perpendicular to the principal ray, and on the other hand, the pulse front 60 of the probe light after being output from the second surface of the prism tilts with respect to a plane perpendicular to the principal ray. In the propagation direction of the probe light, a beam line 56a of the probe light is formed. Even when a diffraction grating is used instead of the prism, the pulse front 60 of the probe light can be tilted.

The degree of temporal tilt of the pulse front 60 tilted by the pulse front tilting unit 32 becomes a time window without change when detecting a pulse terahertz wave according to the measurement principle described later. Therefore, the duration of the terahertz wave is approximately several picoseconds, so that the pulse front 60 of the probe light is preferably provided with a tilt corresponding to several picoseconds or more temporally.

The single terahertz wave time-waveform measuring device 1 works as follows. Pulsed light output from the light source 11 is expanded in beam diameter by the beam diameter adjuster 12 and then input into the separator 13, and two-separated by the separator 13 into a pump light 50 and a probe light 52. The pump light 50 output from the separator 13 is reflected by the mirrors M1 to M3 in order and input into the terahertz wave generator 21. In the terahertz wave generator 21, in response to an input of the pump light 50, a terahertz wave 54 is generated and output. The terahertz wave 54 output from the terahertz wave generator 21 is transmitted through an object to be measured 9 and input into the wave synthesizer 41. On the other hand, the probe light 52 output from the separator 13 is reflected by the mirrors M4 to M8 in order, and the pulse front 60 is tilted by the pulse front tilting unit 32, and then the probe light is linearly polarized by the polarizer 33 and input into the wave synthesizer 41.

The terahertz wave and the probe light input into the wave synthesizer 41 is synthesized coaxially by the wave synthesizer 41, and input into the electro-optic crystal 42 at substantially the same timing. In the electro-optic crystal 42 into which the terahertz wave and the probe light have been input, birefringence is induced along with propagation of the terahertz wave, and the birefringence changes a polarized state of the probe light. Then, the polarized state of the probe light in the electro-optic crystal 42 is detected by the polarizer 33 provided on the light path of the probe optical system, the analyzer 43 provided on the output side of the electro-optic crystal 42, and the photodetector 44 which detects the intensity of the probe light transmitted through the analyzer 43. Thus, the polarized state changes of the probe light in the electro-optic crystal 42 are detected, and eventually, an electric field amplitude of the terahertz wave is detected, and characteristics of the object to be measured 9 are obtained. A spectral device can be configured by applying Fourier transform to signals output from the photodetector 44 into the measured terahertz wave time waveform by an analyzing device not shown.

In the present embodiment, at the time of input into the electro-optic crystal 42, the terahertz wave and the probe light are made coaxial with each other and the pulse front of the probe light tilts with respect to the pulse front of the terahertz wave, so that each position of the probe light on the beam cross-section corresponds to a certain position in the time waveform of the electric field amplitude of the terahertz wave. In addition, the correspondence between these does not change temporally, but is fixed. Therefore, in comparison with the second configuration example, the time waveform does not become inaccurate, and the time resolution is not deteriorated. When obtaining the time waveform of the electric field amplitude of the pulse terahertz wave, only a single pulse is used, so that the time necessary for this is short.

In comparison with the configuration of the first configuration example, the single terahertz wave time-waveform measuring device 1 of the first embodiment is additionally provided with the pulse front tilting unit 32, and the pulse front tilting unit 32 can be formed of a prism or a diffraction grating, so that the time waveform of a pulse terahertz wave can be measured with a single pulse by a comparatively simple configuration. The probe light and the pulse terahertz wave are made incident coaxially on the electro-optic crystal 42, so that alignment is easy, and interaction length can be made long, and the detection sensitivity can be improved.

Figure 9:
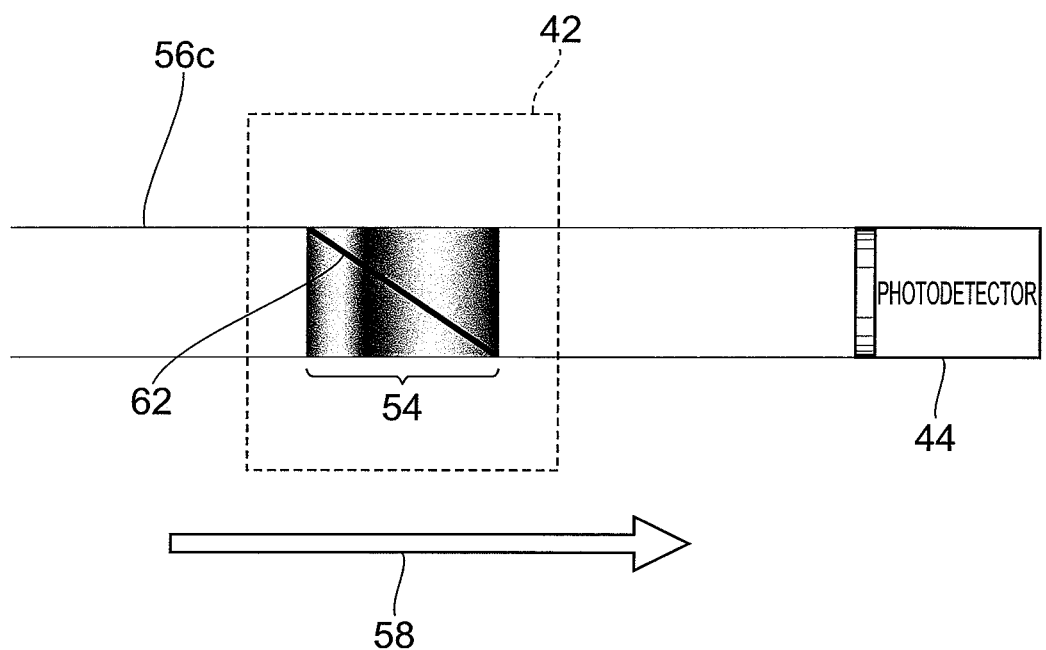
[FIG. 9] is a view showing propagation of a terahertz wave and probe light in an electro-optic crystal 42 included in the single terahertz wave time-waveform measuring device 1 of the first embodiment.

FIG. 9 is a view showing propagations of the terahertz wave and the probe light in the electro-optic crystal 42 included in the single terahertz wave time-waveform measuring device 1 of the first embodiment. The terahertz wave 54 and the probe light 62 whose pulse front is tilted propagate along the propagation direction 58 and forms a beam line 56c of the probe light and the terahertz wave. As shown in this figure, the pulse width of the terahertz wave is on the level of picoseconds, and on the other hand, the pulse width of the probe light is on the level of femtoseconds, and the pulse width of the probe light is several digits smaller than that of the terahertz wave, and the pulse front of the probe light tilts with respect to the pulse front of the terahertz wave.

The pulse terahertz wave output from the pulse terahertz wave generator 21 normally has a beam diameter on the level of centimeters to millimeters. The probe light for detecting the terahertz wave also has a beam diameter on the same level. When the pulse front of the probe light has a tilt equivalent to the duration of the pulse terahertz wave, as shown in FIG. 9, the probe light and the terahertz wave spatially overlap obliquely. In other words, in the propagation direction 58 of the probe light and the pulse terahertz wave (that is, time direction), due to the tilt of the pulse front of the probe light, the probe light overlaps the pulse terahertz at all points of the pulse terahertz wave, however, in the direction perpendicular to the propagation direction 58, the positions are different in the range of the beam diameter. Therefore, by using a photodetector 44 which can detect a one-dimensional or two-dimensional light intensity distribution, temporal changes (temporal information) of the electric field amplitude of the pulse terahertz wave are substituted with a light intensity distribution (spatial information) on the beam cross-section of the probe light, and this spatial information can be detected.

It is also allowed that the pulse front tilting unit 32 changes time delay caused by a tilt of the pulse front of either of the terahertz wave and the probe light when being input into the electro-optic crystal 42 along a predetermined direction on the beam cross-section, and the photodetector 44 detects a one-dimensional distribution of the polarized state changes along the predetermined direction on the beam cross-section of the probe light output from the electro-optic crystal 42. In other words, as shown in FIG. 9, it is allowed that a plurality of light receiving pixels included in the photodetector 44 are one-dimensionally aligned in a predetermined direction, and time delay caused by a tilt of the pulse front of either of the terahertz wave and the probe light changes along the predetermined direction.

The pulse front tilting unit 32 changes time delay caused by a tilt of the pulse front of either of the terahertz wave and the probe light when being input into the electro-optic crystal 42 along a first direction and a second direction orthogonal to each other on the beam cross-section, and it is also preferable that the photodetector 44 detects a two-dimensional distribution of polarized state changes along the first direction and the second direction on the beam cross-section of the probe light output from the electro-optic crystal 42. In other words, the plurality of light receiving pixels included in the photodetector 44 are two-dimensionally aligned in the first direction and the second direction, and time delay caused by a tilt of the pulse front of either of the terahertz wave and the probe light may change along either the first direction or the second direction.

The single terahertz wave time-waveform measuring device 1 of the present embodiment converts temporal information into spatial information, and detects the spatial information by the photodetector 44 to measure temporal changes (temporal information) of the electric field amplitude of the pulse terahertz wave. Therefore, by changing the beam diameter of any of the pulsed light before being two-separated by the separator 13, the probe light, the pump light, and the terahertz wave, the duration and resolution of the information to be obtained (temporal information of pulse terahertz wave) can be changed.

The obtained time waveform of the pulse terahertz wave can be calibrated by adjusting the light path length of the probe optical system by the light path length difference adjuster 31. By adjusting the light path length of the probe optical system, the obtained time waveform of the pulse terahertz wave is spatially shifted. The temporal changes can be converted into light path length adjusting amounts.

Figure 10:
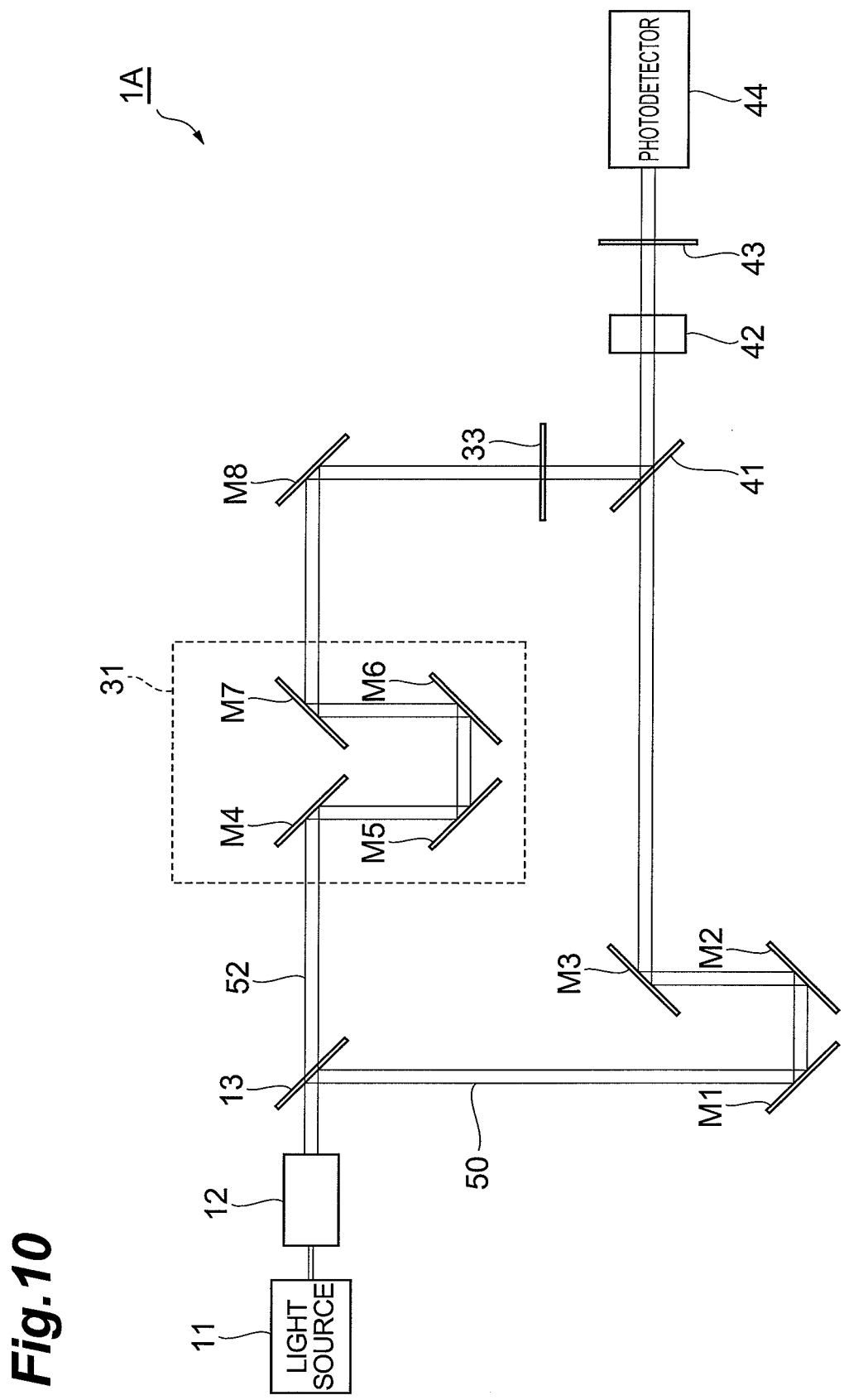
[FIG. 10] is a view showing a device configuration for measuring an actual tilt of a pulse front of the probe light in the single terahertz wave time-waveform measuring device 1 of the first embodiment.

The actual tilt direction and degree of the pulse front of the probe light tilted by the pulse front tilting unit 32 can be measured as follows. FIG. 10 is a view showing a device configuration for measuring an actual tilt of the pulse front of the probe light in the single terahertz wave time-waveform measuring device of the first embodiment. The device 1A shown in this figure is a result of exclusion of the terahertz wave generator 21 and the electro-optic crystal 42 from the configuration of the single terahertz wave time-waveform measuring device 1 shown in FIG. 7, and an object to be measured is not placed on the light path of the terahertz wave optical system.

In this device 1A, the pump light 50 and the probe light 52 which were two-separated by the separator 13 and output are made incident on a detecting surface of the photodetector 44, and on the detecting surface of the photodetector 44, an interference pattern is formed. By imaging this interference pattern by the photodetector 44, based on the region in which this interference pattern is generated and the movement amount of the interference pattern-present region along with the movement of the light path length difference adjuster 31, an actual tilt direction and degree of the pulse front of the probe light tilted by the pulse front tilting unit 32 can be measured. Based on the measurement result, the pulse front tilting unit 32 can be adjusted so that the tilt of the pulse front of the probe light becomes as desired.

(Second Embodiment)

Figure 11:
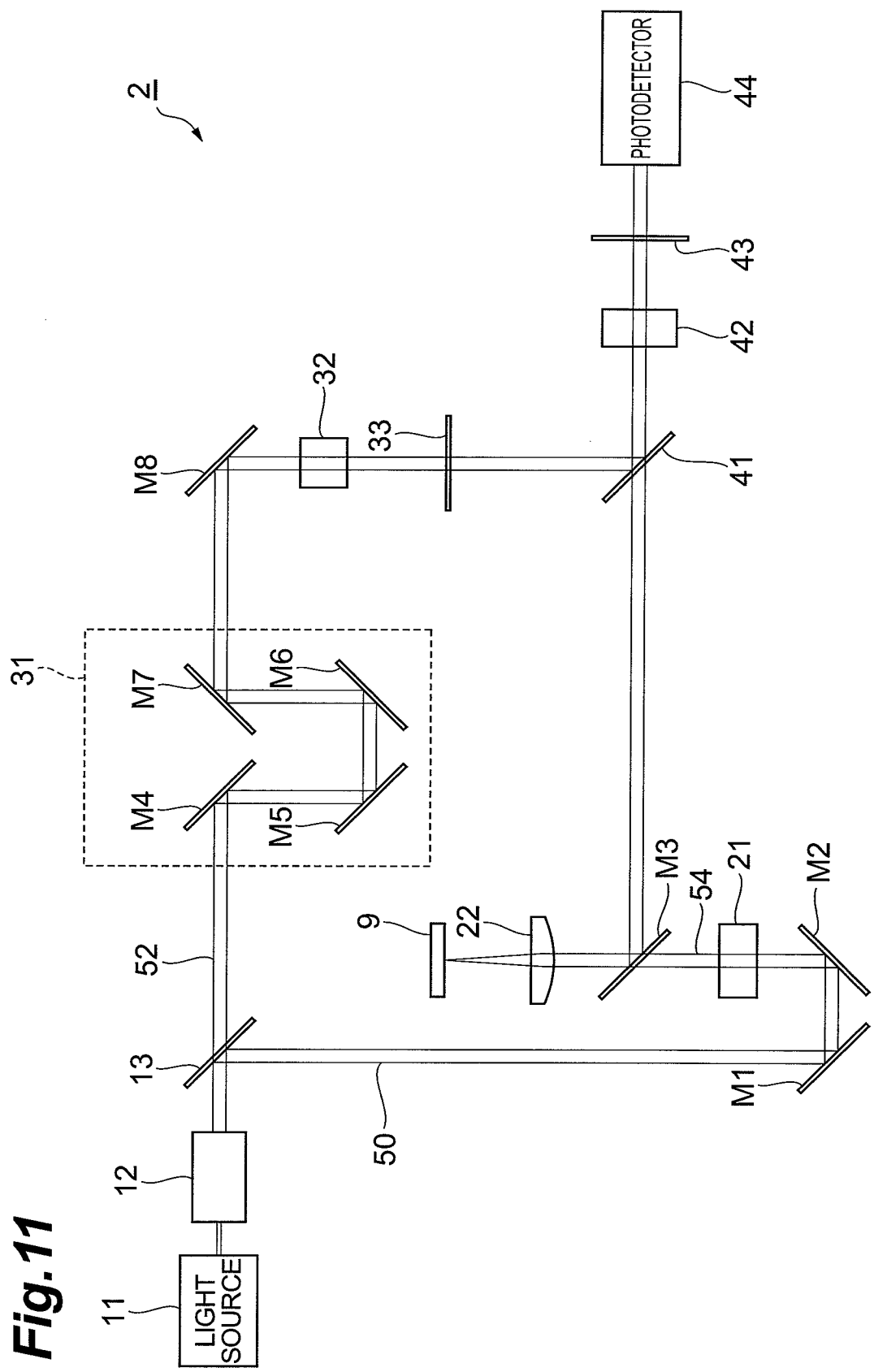
[FIG. 11] is a configuration view of a single terahertz wave time-waveform measuring device 2 of a second embodiment.

Next, a second embodiment of the single terahertz wave time-waveform measuring device of the present invention will be described. FIG. 11 is a configuration view of a single terahertz wave time-waveform measuring device 2 of the second embodiment. The single terahertz wave time-waveform measuring device 2 shown in this figure measures an object to be measured 9 by single terahertz wave time waveform measurement by using a terahertz wave, and includes a light source 11, a beam diameter adjuster 12, a separator 13, a terahertz wave generator 21, a cylindrical lens 22, a light path length difference adjuster 31, a pulse front tilting unit 32, a polarizer 33, a wave synthesizer 41, an electro-optic crystal 42, an analyzer 43, a photodetector 44, and mirrors M1 to M8.

In comparison with the configuration of the single terahertz wave time-waveform measuring device 1 of the first embodiment shown in FIG. 7, the single terahertz wave time-waveform measuring device 2 of the second embodiment shown in FIG. 11 is different in that the mirror M3 is a half mirror, the terahertz wave generator 21 is disposed between the mirror M2 and the half mirror M3, and a cylindrical lens 22 is further provided, and an object to be measured 9 is placed at a light condensing position of this cylindrical lens 22. This cylindrical lens 22 operates as a condenser which condenses and irradiates the terahertz wave 54 output from the terahertz wave generator 21 in a line onto the object to be measured 9, and also operates as a collimator which collimates the terahertz wave reflected by the object to be measured 9 and outputs it to the wave synthesizer 41.

This single terahertz wave time wave-form measuring device 2 works as follows. Pulsed light output from the light source 11 is expanded in beam diameter by the beam diameter adjuster 12 and then input into the separator 13, and two-separated by the separator 13 into a pump light 50 and a probe light 52. The pump light 50 output from the separator 13 is reflected by the mirrors M1 and M2 in order and input into the terahertz wave generator 21. In the terahertz wave generator 21, the terahertz wave 54 is generated in response to an input of the pump light 50 and output. The terahertz wave 54 which was output from the terahertz wave generator 21 and transmitted through the half mirror M3 is condensed in a line and irradiated onto the object to be measured 9 by the cylindrical lens 22. The terahertz wave reflected by the object to be measured 9 according to this irradiation is collimated by the cylindrical lens 22, reflected by the half mirror M3, and input into the wave synthesizer 41.

The terahertz wave and the probe light input into the wave synthesizer 41 are synthesized coaxially by the wave synthesizer 41, and input into the electro-optic crystal 42 at the same timing. In the electro-optic crystal 42 in which the terahertz wave and the probe light have been input, birefringence is induced along with propagation of the terahertz wave, and the birefringence changes the polarized state of the probe light. Then, the polarized state of the probe light in the electro-optic crystal 42 is detected as light intensity by the polarizer 33 provided on the light path of the probe optical system, the analyzer 43 provided on the output side of the electro-optic crystal 42, and the photodetector 44 which detects the intensity of the probe light transmitted through the analyzer 43. Thus, polarized state changes of the probe light in the electro-optic crystal 42 are detected, and eventually, the electric field amplitude of the terahertz wave is detected, and characteristics of the object to be measured 9 are obtained.

In the present embodiment, at the time of the input into the electro-optic crystal 42, the terahertz wave and the probe light are made coaxial, and the pulse front of the probe light tilts with respect to the pulse front of the terahertz wave, so that each position on a beam cross-section of the probe light corresponds to a certain position in the time waveform of the electric field amplitude of the terahertz wave. In addition, the correspondence between these does not change temporally but is fixed. Therefore, in comparison with the second configuration example, the time waveform does not become inaccurate, and the time resolution is not deteriorated. When obtaining the time waveform of the electric field amplitude of the pulse terahertz wave, only a single pulse is used, so that the time necessary for this is short.

In comparison with the first embodiment in which the terahertz wave is transmitted through the object to be measured 9, the second embodiment is different in that the terahertz wave is reflected by the object to be measured 9. Therefore, the second embodiment is preferable for inspecting a film thickness of a coating film as an object to be measured 9. In other words, the coating film changes in film thickness along with solvent volatilization, etc., with elapse of time after formation of the film. When the coating surface is irradiated with a pulse terahertz wave and a pulse terahertz wave reflected from the metal on the back side of the coating film is measured, the pulse terahertz wave depending on the thickness and contained components of the coating film can be observed. In detail, in a state where the coating film immediately after being coated is thick, the length of the light path in which the pulse terahertz wave passes becomes effectively long, and attenuation also increases. On the other hand, after an appropriate time elapses, according to reduction in thickness of the coating film due to solvent volatilization, etc., the reflected wave of the pulse terahertz wave is detected temporarily earlier with smaller attenuation. Accordingly, by observing reflection of the pulse terahertz wave, changes in film thickness of the coating film can be investigated. Thus, the single terahertz wave time-waveform measuring device is especially effective for observing a transitional change.

Figure 12:
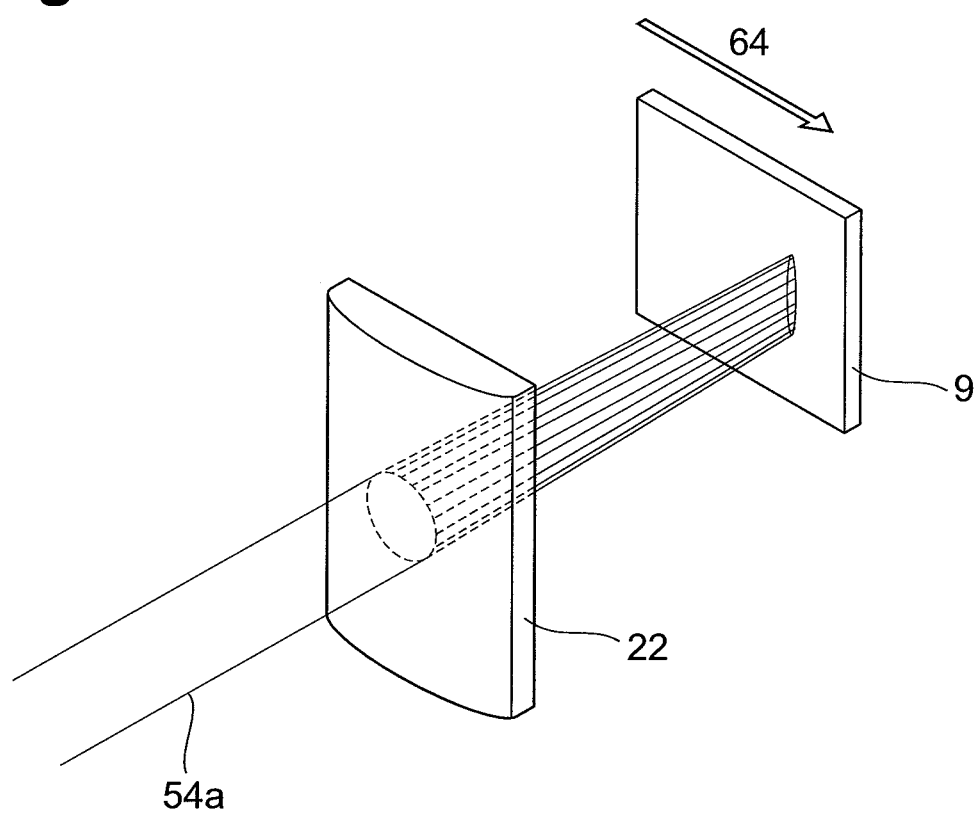
[FIG. 12] is a view showing condensed irradiation of a terahertz wave onto an object to be measured 9 by a cylindrical lens 9 in the single terahertz wave time-waveform measuring device 2 of the second embodiment.

In the second embodiment, by using a photodetector 44 which can detect a two-dimensional light intensity distribution, the following measurement can also be performed. That is, in condensed irradiation of the terahertz wave onto the object to be measured 9 by the cylindrical lens 9, as shown in FIG. 12, the terahertz wave (pulse terahertz wave 54a) is condensed in a line and irradiated onto the object to be measured 9 by the cylindrical lens 9, and the object to be measured 9 is scanned in a direction 64 perpendicular to the line. By condensed irradiation in a line of the terahertz wave onto the object to be measured 9, at each position of the line on the object to be measured 9, the time waveform of the electric field amplitude of the terahertz wave can be measured with a single pulse. By scanning the object to be measured 9 in the direction 64 perpendicular to the line, information in a wide range of the object to be measured 9 can be obtained.

(Third Embodiment)

Figure 13:
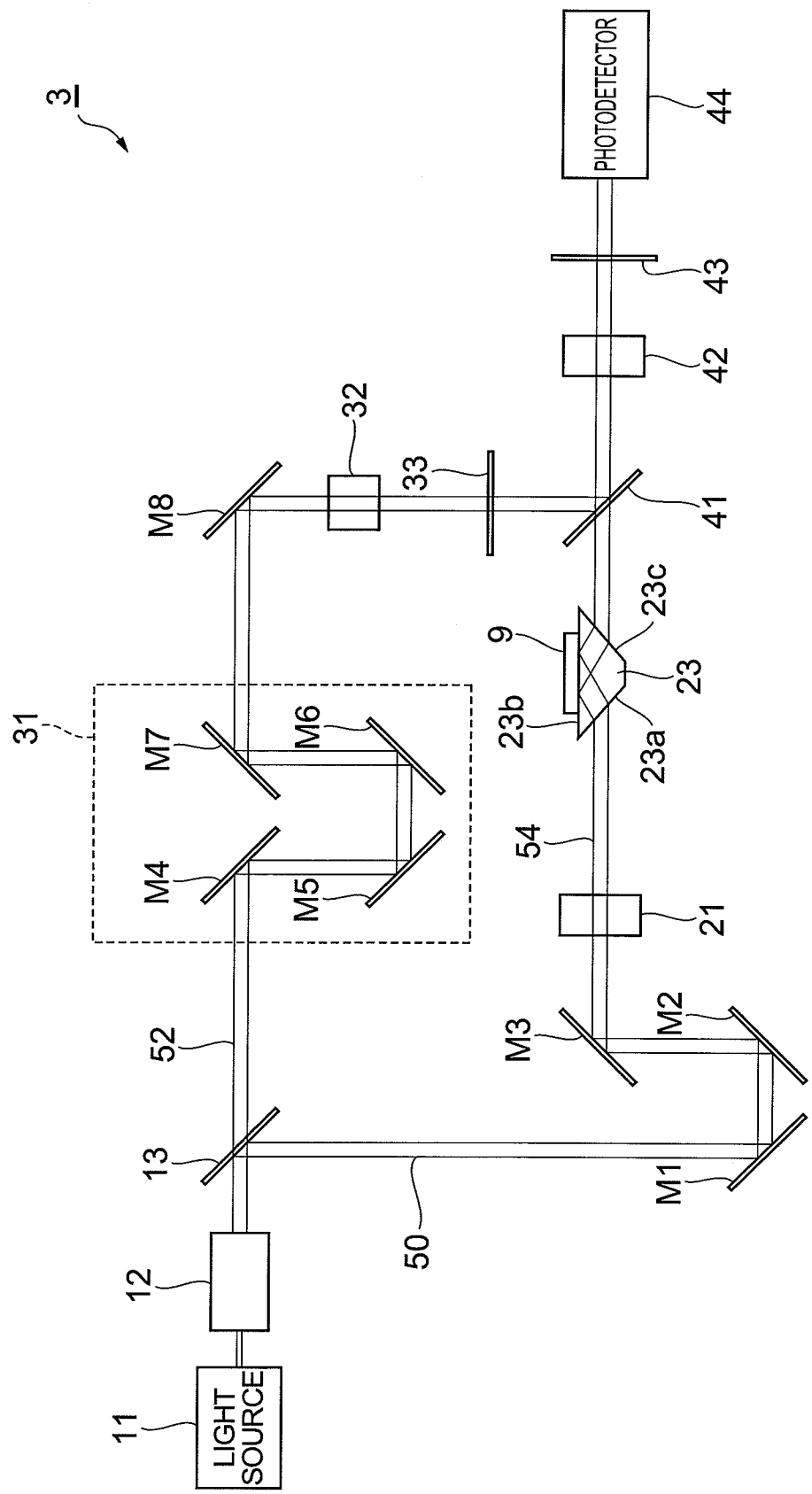
[FIG. 13] is a configuration view of a single terahertz wave time-waveform measuring device 3 of a third embodiment.

Next, a third embodiment of a single terahertz wave time-waveform measuring device of the present invention will be described. FIG. 13 is a configuration view of a single terahertz wave time-waveform measuring device 3 of the third embodiment. The single terahertz wave time-waveform measuring device 3 shown in this figure acquires information on an object to be measured 9 by using a terahertz wave, and includes a light source 11, a beam diameter adjuster 12, a separator 13, a terahertz wave generator 21, a prism 23, a light path length difference adjuster 31, a pulse front tilting unit 32, a polarizer 33, an electro-optic crystal 42, an analyzer 43, a photodetector 44, and mirrors M1 to M8.

In comparison with the configuration of the single terahertz wave time-waveform measuring device 1 of the first embodiment shown in FIG. 7, the single terahertz wave time-waveform measuring device 3 of the third embodiment shown in FIG. 13 is different in that it further includes a prism 23 on which an object to be measured 9 is placed. The prism 23 is a dove prism which propagates inside a terahertz wave 54 which was input into a first surface 23a from the outside and then totally reflects the terahertz wave by a second surface 23b, and propagates the totally-reflected terahertz wave inside and then outputs it to the outside from a third surface 23c, and the principal rays of the terahertz wave 54 input into the first surface 23a and the terahertz wave output from the third surface 23c are on the same straight line. The object to be measured 9 is placed on the second surface 23b of the prism 23.

In this single terahertz wave time-waveform measuring device 3, the terahertz wave 54 output from the terahertz wave generator 21 propagates inside the prism 23 and is totally reflected by the second surface 23b of the prism 23. At the time of this total reflection, an evanescent component is present at a portion of the object to be measured 9 near the second surface 23b. Accordingly, the terahertz wave after being totally reflected by the second surface 23b of the prism 23 acquires information of the portion of the object to be measured 9 near the second surface 23b. Then, the totally-reflected terahertz wave propagates inside the prism 23 and is output to the outside from the third surface 23c of the prism 23. The terahertz wave output from the prism 23 is input into the wave synthesizer 41 together with the probe light which passed through a probe optical system.

The terahertz wave and the probe light input into the wave synthesizer 41 are synthesized coaxially by the wave synthesizer 41 and input into the electro-optic crystal 42 at substantially the same timing. In the electro-optic crystal 42 in which the terahertz wave and the probe light have been input, birefringence is induced along with propagation of the terahertz wave, and the birefringence changes the polarized state of the probe light. Then, the polarized state of the probe light in the electro-optic crystal 42 is detected as light intensity by the polarizer 33 provided on the optical path of the probe optical system, the analyzer 43 provided on the output side of the electro-optic crystal 42, and the photodetector 44 which detects the intensity of the probe light transmitted through the analyzer 43. Thus, polarized state changes of the probe light in the electro-optic crystal 42 are detected, and eventually, the electric field amplitude of the terahertz wave is detected, and characteristics of the object to be measured 9 are obtained.

Also in the present embodiment, at the time of input into the electro-optic crystal 42, the terahertz wave and the probe light are made coaxial, and the pulse front of the probe light tilts with respect to the pulse front of the terahertz wave, so that each position on the beam cross-section of the probe light corresponds to a certain position in the time waveform of the electric field amplitude of the terahertz wave. This correspondence does not change temporally, but is fixed. Therefore, in comparison with the second configuration example, the time waveform does not become inaccurate, and the time resolution is not deteriorated. To obtain the time waveform of the electric field amplitude of the pulse terahertz, only a single pulse is used, so that the time necessary for this is short. Particularly, in the present embodiment, only a portion of the object to be measured 9 near the second surface 23b of the prism 23 can be selectively measured.

(Fourth Embodiment)

Figure 14:
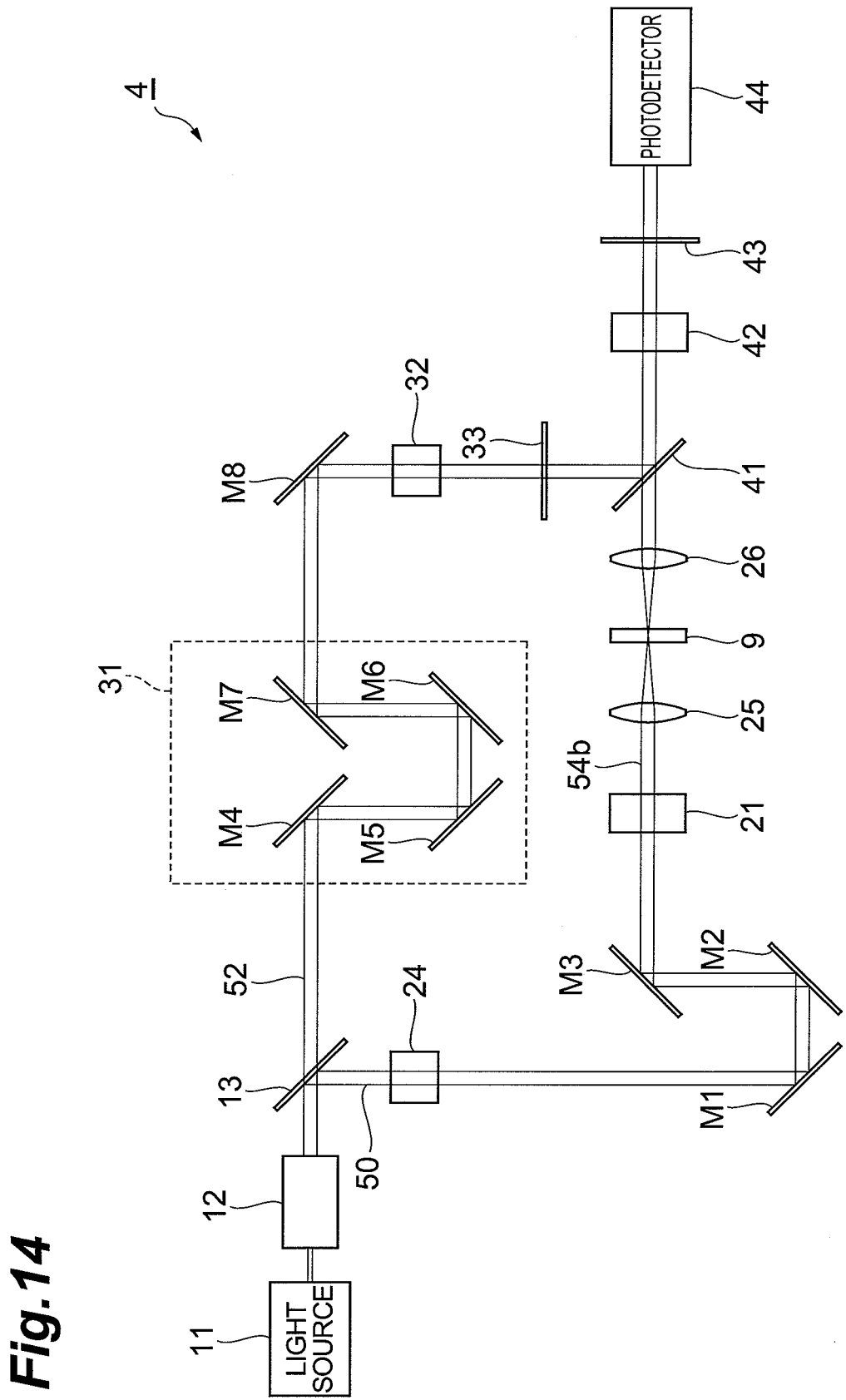
[FIG. 14] is a configuration view of a single terahertz wave time-waveform measuring device 4 of a fourth embodiment.

Next, a fourth embodiment of a single terahertz wave time-waveform measuring device of the present invention will be described. FIG. 14 is a configuration view of a single terahertz wave time-waveform measuring device of the fourth embodiment. The single terahertz wave time-waveform measuring device 4 shown in this figure acquires information on an object to be measured 9 by using a terahertz wave, and includes a light source 11, a beam diameter adjuster 12, a separator 13, a terahertz wave generator 21, a pulse front tilting unit 24, a lens 25, a lens 26, a light path length difference adjuster 31, a pulse front tilting unit 32, a polarizer 33, a wave synthesizer 41, an electro-optic crystal 42, an analyzer 43, a photodetector 44, and mirrors M1 to M8.

In comparison with the configuration of the single terahertz wave time-waveform measuring device 1 of the first embodiment shown in FIG. 7, the single terahertz wave time-waveform measuring device 4 of the fourth embodiment shown in FIG. 14 is different in that it further includes a pulse front tilting unit 24 which is provided on the light path of the pump optical system and tilts the pulse front of the pump light, and further includes a lens 25 and a lens 26 provided so as to sandwich the object to be measured 9 therebetween on the light path of the terahertz wave optical system.

The pulse front tilting unit 24 provided on the light path of the pump optical system tilts the pulse front of the pump light 50. On the other hand, the pulse front tilting unit 32 provided on the light path of the probe optical system tilts the pulse front of the probe light 52. By tilting the pulse fronts of the pump light 50 and the probe light 52 by the pulse front tilting units 24 and 32, time delay caused by tilts of the pulse fronts of the terahertz wave and the probe light when being input into the electro-optic crystal 42 changes along a first direction and a second direction orthogonal to each other on the beam cross-section.

The photodetector 44 detects a two-dimensional distribution of polarized state changes along the first direction and the second direction on the beam cross-section of the probe light output from the electro-optic crystal 42. In other words, a plurality of light receiving pixels included in the photodetector 44 are two-dimensionally aligned in the first direction and the second direction, and along either direction of the first direction and the second direction, time delay caused by tilts of the pulse fronts of the terahertz wave and the probe light change.

By tilting the pulse front of the pump light 50 by the pulse front tilting unit 24 provided on the light path of the pump optical system, the pulse front of the terahertz wave 54b also tilts. Therefore, for example, by measuring a transmissivity of the object to be measured 9 by using the terahertz wave 54b whose pulse front is tilted, the terahertz wave can measure a transitional change in transmissivity of the object to be measured 9.

By proving the terahertz wave by a probe light having a pulse front which tilts in a direction different from the tilting direction of the pulse front of the terahertz wave, the time waveform of the pulse terahertz wave with a tilting pulse front can be acquired with a single pulse in the entire range, and a transitional response of the object to be measured 9 can be acquired at one time by the two-dimensional photodetector 44.

A measuring device including an exciting device which causes a transitional change of the object to be measured 9 is also preferable. As this exciting device, a femtosecond laser beam, etc., can be used.

Further, spatial information obtained in the present embodiment is 0-dimensional. Therefore, the interval between the lens 25 and the lens 26 provided on the light path of the terahertz wave optical system is set to be equal to the sum of focal lengths of these, and by disposing the object to be measured 9 at the focal point, the terahertz wave 54*b* output from the terahertz wave generator 21 is condensed to the object to be measured 9 by the lens 25, whereby the measuring efficiency can be improved.

The invention claimed is:

1. A single terahertz wave time-waveform measuring device comprising:
   a light source which outputs pulsed light;
   a separator which two-separates the pulsed light output from the light source, and outputs one of the two-separated pulsed lights as a pump light and the other as a probe light;
   a terahertz wave generator which generates and outputs a terahertz wave by receiving an input of the pump light output from the separator;
   a wave synthesizer which receives inputs of the terahertz wave which was output from the terahertz wave generator and transmitted through or reflected by an object to be measured and the probe light which was output from the separator and reached, and synthesizes coaxially and outputs the terahertz wave and the probe light;
   an electro-optic crystal which receives inputs of the terahertz wave and the probe light output from the wave synthesizer, induces birefringence along with propagation of the terahertz wave, and changes a polarized state of the probe light by the birefringence and outputs the probe light;
   a pulse front tilting unit which makes pulse fronts of the terahertz wave and the probe light when being input into the electro-optic crystal nonparallel to each other by tilting the pulse front of any of the pump light, the terahertz wave, and the probe light; and
   a detecting device which detects a distribution of polarized state changes on a beam cross-section of the probe light output from the electro-optic crystal.

2. The single terahertz wave time-waveform measuring device according to claim 1, further comprising a light path length difference adjuster which adjusts a difference between a light path of the pump light and the terahertz wave from the separator to the wave synthesizer and a light path of the probe light from the separator to the wave synthesizer.

3. The single terahertz wave time-waveform measuring device according to claim 1, further comprising a beam diameter adjuster which adjusts both or either of beam diameters of the terahertz wave and the probe light when being input into the electro-optic crystal.

4. The single terahertz wave time-waveform measuring device according to claim 1, wherein
   the pulse front tilting unit changes time delay caused by a tilt of the pulse front of either of the terahertz wave and the probe light when being input into the electro-optic crystal along a predetermined direction on a beam cross-section, and
   the detecting device detects a one-dimensional distribution of polarized state changes along the predetermined direction on the beam cross-section of the probe light output from the electro-optic crystal.

5. The single terahertz wave time-waveform measuring device according to claim 1, wherein
   the pulse front tilting unit changes time delay caused by a tilt of the pulse front of either of the terahertz wave and the probe light when being input into the electro-optic crystal along a first direction and a second direction on a beam cross-section, and
   the detecting device detects a two-dimensional distribution of polarized state changes along the first direction and the second direction on the beam cross-section of the probe light output from the electro-optic crystal.

6. The single terahertz wave time-waveform measuring device according to claim 1, further comprising:
   a condenser which condenses and irradiates the terahertz wave output from the terahertz wave generator in a line onto the object to be measured; and
   a collimator which collimates the terahertz wave transmitted through or reflected by the object to be measured and outputs the terahertz wave to the wave synthesizer.

\* \* \* \* \*